(12) United States Patent
Plank (10) Patent No.: US 9,738,920 B2
(45) Date of Patent: Aug. 22, 2017

(54) IN VITRO METHOD FOR ESTIMATING IN VIVO PROTEIN DIGESTIBILITY

(71) Applicant: General Mills, Inc., Minneapolis, MN (US)

(72) Inventor: David W. Plank, Golden Valley, MN (US)

(73) Assignee: General Mills, Inc., Minneapolis, MN (US)

( * ) Notice: Subject to any disclaimer, the term of this patent is extended or adjusted under 35 U.S.C. 154(b) by 0 days.

(21) Appl. No.: 14/599,050

(22) Filed: Jan. 16, 2015

(65) Prior Publication Data

US 2016/0208309 A1  Jul. 21, 2016

(51) Int. Cl.
*C12Q 1/37* (2006.01)
*G01N 21/75* (2006.01)

(52) U.S. Cl.
CPC .............. *C12Q 1/37* (2013.01); *G01N 21/75* (2013.01)

(58) Field of Classification Search
CPC ...................................................... C12Q 1/37
See application file for complete search history.

(56) References Cited

U.S. PATENT DOCUMENTS

| 6,750,035 B1 | 6/2004 | Schasteen et al. |
| 7,393,659 B2 | 7/2008 | Johns et al. |
| 2011/0143445 A1 | 6/2011 | Daniels et al. |
| 2014/0178903 A1 | 6/2014 | Sousa et al. |
| 2014/0260562 A1 | 9/2014 | Motlagh |

FOREIGN PATENT DOCUMENTS

WO    2014130007 A1    8/2014

OTHER PUBLICATIONS

Hill et al. JBC, 1962, 237(2):389-396.*
Chang et al., 1990, J. Agric. Food Chem., 38(4):1016-1018.*
Sindayikengera Severin et al. J Zhejiang Univ. Science B, 2006, 7(2):90-98.*
McDonough et al., "In Vitro Assay for Protein Digestibility: Interlaboratory Study," Abstract, Journal of the Association of Official Analytical Chemists, vol. 73, No. 4, Jul./Aug. 1990, pp. 622-625.
Rozan et al., "In Vivo and in Vitro Digestibility of Soybean, Lupine, and Rapeseed Meal Proteins after Various Technological Processes," Abstract, Journal of Agricultural and Food Chemistry, vol. 45, No. 5, May 1997, pp. 1762-1769.
Golden et al., "Amino Acid, Fatty Acid, and Carbohydrate Content of *Artocarpus altilis* (Breadfruit)," Journal of Chromatographic Science, vol. 39, No. 6, Jun. 30, 2001, pp. 243-250.
International Patent Application No. PCT/US2016/013247, International Search Report and Written Opinion mailed Mar. 25, 2016, 14 pages.
Schweet, "The Quantitative Determination of Proline and Pipecolic Acid with Ninhydrin," Journal of Biological Chemistry, vol. 208, Jun. 1, 1954, pp. 603-614.
Uberti et al., "Development of an in vitro model to simulate the gastrointestinal digestion and absorption of stabilizing agents," InBIO Web of Conferences, vol. 3, Nov. 4, 2014, pp. 1-4.

* cited by examiner

*Primary Examiner* — Bin Shen
(74) *Attorney, Agent, or Firm* — Fredrikson & Byron, P.A.

(57) ABSTRACT

An analysis technique can be performed to quantify the digestible protein content of a protein-containing sample outside the body of a living organism. Traditionally, protein digestibility is evaluated in vivo, for example using a rat subject to measure protein digestibility after being fed the protein-containing sample. In some examples, an in vitro technique involves enzymatically digesting the protein-containing sample to simulate digestion that would occur inside a mammalian body. The sample can then be optically analyzed to measure the amount of reactive amine present in the sample, which can provide an indication of the amount of amino acid released during digestion. In some examples, the measured reactive amine value is adjusted to account for the stronger and/or weaker optical response of certain amino acids due to their relative reactivity with an optical tagging agent. Thereafter, an in vivo protein digestibility value can be calculated based on adjusted amine concentration.

29 Claims, 2 Drawing Sheets

IN VITRO METHOD FOR ESTIMATING IN VIVO PROTEIN DIGESTIBILITY

TECHNICAL FIELD

This disclosure relates to the quantification of digestible protein, including the quantification of digestible protein in consumable food sources.

BACKGROUND

Protein is an important nutritional component for mammalians. Unlike most plants and microorganisms that can biosynthesize all twenty standard amino acids needed for health and reproduction, typical mammals cannot synthesize all amino acids needed for survival. These amino acids that cannot be synthesized are referred to as essential amino acids and are required to be obtained through the diet. Amino acids are provided in the diet by ingesting protein-containing foods. Digestive enzymes can hydrolyze peptide bonds in the ingested proteins to release individual amino acids. These amino acids are free to be absorbed into the body, providing nutritional benefits.

In addition to providing required nutrients, foods high in protein are increasingly desired by consumers for a variety of others reasons. When consumed, foods high in protein can help satisfy an individual's feeling of hunger for a longer period of time than when consuming comparatively lower protein foods. This helps limit overconsumption of food and can help balance a healthy lifestyle. Further, a high protein diet can support muscle growth and maintenance for active individuals.

Given the nutritional and lifestyle benefits of a high protein diet, food manufacturers are providing increasing numbers of high protein products to the consuming public. Before marketing these products, manufacturers typically first quantify the amount of digestible protein in each product. Different proteins digest to different extents within the mammalian digestion system and, correspondingly, provide different nutritional benefits. It is the amount of digestible protein that is usually reported on food packaging labels.

Traditionally, protein digestibility has been evaluated in vivo using rat subjects to measure the amount of protein digestion that occurs when fed a protein-containing product. The total amount of nitrogen in the food product is measured before being fed to a rat subject and compared to the total amount of nitrogen in the feces produced by the rat. The nitrogen uptake by the rat provides a measure of the amount of digestible protein in the product. While yielding suitable results, this in vivo measurement process is both costly and time consuming. For example, a typical in vivo protein measurement using a rat subject can take 30 days or more to perform.

SUMMARY

In general, this disclosure is directed to techniques for measuring the amount of digestible protein in protein-containing products. The techniques can be performed in vitro (outside of a living organism) to generate digestible protein measurements equivalent to what would have been produced were a protein-containing sample evaluated in vivo (e.g., measuring consumption and excretion of a living organism). For example, data generated from in vitro analysis can be adjusted using empirical in vivo data to provide in vivo protein digestibility values from the in vitro analysis.

By providing an in vitro measurement technique that yields protein digestibility results equivalent to what would have been provided from in vivo measurement, a comparatively rapid and inexpensive method for obtaining protein digestibility results can be provided that avoids the use of living organisms for testing.

Although the specific technique can vary, in some examples, the digestible protein content of a sample is determined by enzymatically digesting a protein-containing sample with an enzyme that simulates mammalian protein digestion. For example, the protein-containing sample can be enzymatically digested with a combination of enzymes that simulate gastric digestion within a mammal as well as intestinal digestion within the mammal. Enzymatic digestion of the protein-containing sample can hydrolyze proteins contained within the sample and release amino acids consistent with how the proteins would be hydrolyzed within a mammalian body. The released amino acids can represent the portion of the protein that would be expected to be digested in the mammalian body while the remainder of the protein may not be expected to digest in the body.

In some examples, the hydrolyzed protein solution resulting from enzymatic digestion is optically analyzed to quantify the amount of amino acid released from the protein-containing sample following enzymatic digestion. When amino acid is enzymatically cleaved from a protein backbone, the resulting free amino acid contains an amine functional group where previously joined to the protein while the protein contains a carboxylic acid functional group where previously joined to the amino acid. By adding a spectroscopic agent to the hydrolyzed protein solution that reacts with the amine functional group or the carboxylic acid functional group, the amount of amino acid released during enzymatic digestion can be optically evaluated. For example, a spectroscopic agent that reacts with one of the amino acid functional group and carboxylic acid functional group can be added to the hydrolyzed protein solution and the solution thereafter optically analyzed to measure the amount of amino acid functional groups or carboxylic acid functional groups in the solution.

To determine an in vivo protein digestibility value from the optical analysis data, the measured amount of amino acid functional groups or carboxylic acid functional groups in the hydrolyzed protein solution can be adjusted based on the type and amount of different amino acids in the protein-containing sample under analysis. For example, the protein-containing sample may be separately assayed to determine which amino acids are present in the protein-containing sample and the relative concentration of each specific amino acid in the sample. Using this amino acid concentration data, the measured amount of amino acid functional groups or carboxylic acid functional groups can be increased or decreased to compensate for expected relative over reactivity or under reactivity with the spectroscopic agent. For example, in instances where the amino acid and/or cleaved protein provides multiple sites that react with the spectroscopic agent, optical analysis of the hydrolyzed protein solution may indicate the presence of more free amino acids than are actually present. Adjusting the optical analysis data based on the relative concentration of the different amino acids in the protein-containing sample and their relative reactivity with the spectroscopic agent can correct the optical analysis data for over and/or under reactivity with the agent.

After adjusting the optical analysis data that provides an indication of the amount of amino acid released from the protein-containing sample during simulated digestion, the in vitro data can be correlated with in vivo protein digestion data. For example, the adjusted in vitro measurements can be correlated with in vivo data relating different in vivo protein digestibility values to different in vitro amino acid concentration values. In this manner, the in vitro concentration data can provide an accurate measure of in vivo protein digestion, were the protein-containing sample to be evaluated using in vivo techniques.

In one example, a method is described that includes combining a sample containing a protein with at least one enzyme configured to simulate mammalian protein digestion, thereby at least partially hydrolyzing the protein and producing therefrom a hydrolyzed protein solution. The method further involves adding a spectroscopic agent to the hydrolyzed protein solution that reacts with at least one of amine terminal and carboxylic terminal groups in the hydrolyzed protein solution, thereby forming an optical analysis solution, and optically analyzing the optical analysis solution and determining therefrom a value indicative of at least one of a concentration of reactive amine groups in the optical analysis solution and a concentration of reactive carboxylic acid groups in the optical analysis solution. The method further involves adjusting the value indicative of at least one of the concentration of reactive amine groups and the concentration of reactive carboxylic acid groups using amino acid concentration data for the sample to determine at least one of an adjusted amine concentration value and an adjusted carboxylic acid concentration value. In addition, the method includes determining an in vivo protein digestibility value for the sample based on the at least one of the adjusted amine concentration value and the adjusted carboxylic acid concentration value using data that relates adjusted amine concentration values or adjusted carboxylic acid concentration values to in vivo digestibility values.

In another example, a method is described that includes mixing a sample containing a protein with pepsin to simulate mammalian gastric digestion and generating therefrom a simulated gastrically digested sample and mixing the simulated gastrically digested sample with trypsin and chymotrypsin to simulate mammalian intestinal digestion and generating therefrom a simulated intestinally digested sample. The method includes adding a spectroscopic agent to the simulated intestinally digested sample that reacts with at least one of amine terminal and carboxylic terminal groups in the simulated intestinally digested sample, thereby forming an optical analysis solution, and optically analyzing the optical analysis solution and determining therefrom a value indicative of at least one of a concentration of reactive amine groups in the optical analysis solution and a concentration of reactive carboxylic acid groups in the optical analysis solution. The method further includes adjusting the value indicative of at least one of the concentration of reactive amine groups and the concentration of reactive carboxylic acid groups using amino acid concentration data for the sample to determine at least one of an adjusted amine concentration value and an adjusted carboxylic acid concentration value. In addition, the method involves determining an in vivo protein digestibility value for the sample based on the at least one of the adjusted amine concentration value and the adjusted carboxylic acid concentration value using data that relates adjusted amine concentration values or adjusted carboxylic acid values to in vivo digestibility values.

The details of one or more examples are set forth in the accompanying drawings and the description below. Other features, objects, and advantages will be apparent from the description and drawings, and from the claims.

DETAILED DESCRIPTION

In general, this disclosure relates to the quantification of digestible protein in protein-containing products. The term digestible protein generally refers to that protein in the protein-containing product that provides constituent amino acids for metabolization and utilization by an animal upon consumption. Further, the term protein generally refers to any complex organic macromolecule that is composed of one or more chains of amino acids. The digestibility of protein is a function of the amount of protein in the product and the ability of the digesting animal to metabolize the protein. For example, digestible protein can breakdown within the digestive system of the consuming animal and release free amino acids that can absorb into the body. In contrast to digestible protein, indigestible protein does not breakdown within the digestion system of the animal and therefore does not release amino acids for metabolization and utilization. Rather, such indigestible protein can pass through the animal's digestive system and into their excrement following consumption of the protein-containing product.

A wide variety of products may contain digestible protein (e.g., both digestible protein and indigestible protein) that is desirably quantified. Example products include consumable foods, beverages, and/or nutritional supplements. In some examples, a consumable product containing digestible protein desirably quantified is a consumable product that is intended for mammalian consumption, such as by humans and/or animals (e.g., cats, dogs, horses, cows). Specific examples of products that may include digestible protein include animal feed, vitamins, cereal, granola bars, bakery items (e.g., bread, cookies, brownies, muffins), yogurt, and any other food, beverage, or supplement containing protein desirably quantified. The digestible protein present in a product may be naturally occurring due to the addition of protein-containing ingredients to the product. Additionally or alternatively, the digestible protein present in a product may be deliberately added, e.g., by adding a protein supplement to the product. Sources of protein that may be added to a product to enhance protein content include, but are not limited to, wheat gluten, milk protein, soy protein and eggs in any form including whole eggs, egg whites, powdered eggs, powdered egg whites and the like.

Independent of the source of protein present in a product, the product may contain any suitable amount of digestible protein. For example, a product may contain from 0.1 weight percent digestible protein to 95 weight percent digestible protein, such as from 5 weight percent digestible protein to 60 weight percent digestible protein, or from 10 weight percent digestible protein to 50 weight percent digestible protein. The amount of indigestible protein in such products will vary depending on the type and amount of proteins present in the product. In some cases, the indigestible protein will range from 0 weight percent to 70 weight percent of the food product. The weight percentage of digestible protein present in a product (and, correspondingly, the amount of indigestible protein) may be determined in accordance with the techniques of the present disclosure.

Figure 1:
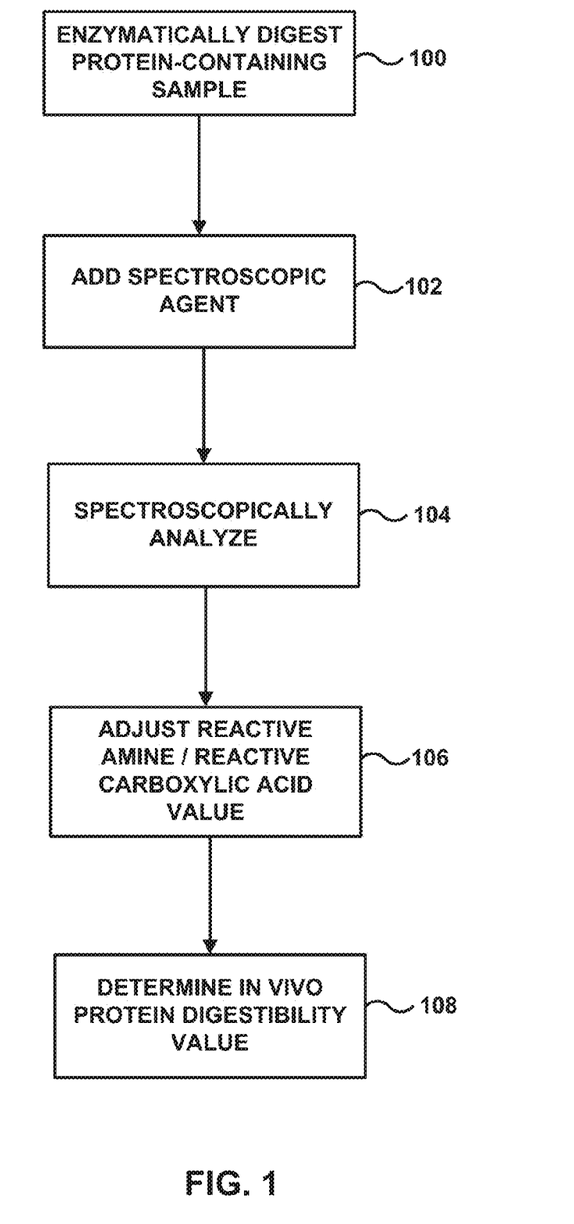
FIG. 1 is a flow diagram illustrating an example process for determining the digestible protein content of a product.

FIG. 1 is a flow diagram illustrating an example process for determining the digestible protein content of a product. The process starts by obtaining a sample of a product containing protein (also referred to herein as a "protein-containing sample") and combining the sample with one or more enzymes configured to simulate in vivo digestion of the protein-containing sample (100). The enzymes may be selected to imitate enzymatic breakdown that would otherwise occur in the digestion system of a mammalian subject (e.g., human, rat), were the protein-containing sample to be ingested, thereby simulating in vivo digestion. For example, the enzymes used may be those found in the digestion system of a mammalian subject and/or enzymes providing substantially similar enzymatic behavior to those found in the mammalian subject. Addition of the one or more enzymes to the protein-containing sample can digest the digestible protein portion of the sample while leaving the indigestible portion of the sample substantially or completely undigested. The one or more enzymes can digest a portion of the protein-containing sample by enzymatically breaking chemical bonds in the protein. For example, the one or more enzymes can hydrolyze peptide bonds releasing, among other things, free amino groups.

Figure 2:
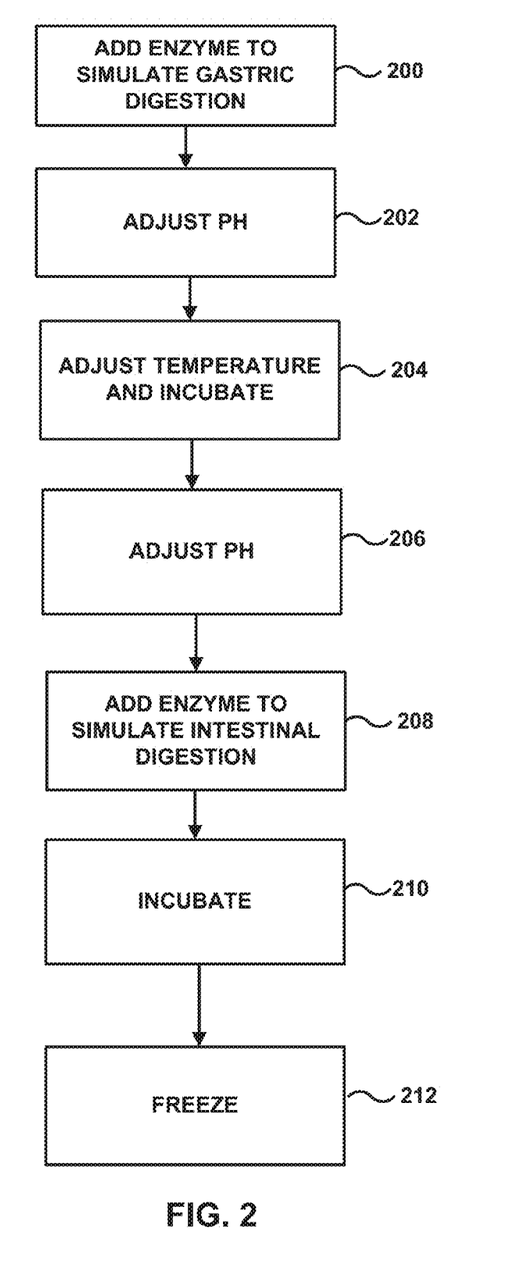
FIG. 2 is a flow diagram illustrating an example process for enzymatically digesting a protein-containing sample that can be used in the example technique of FIG. 1.

Example enzymes and conditions for enzymatically digesting a protein-containing sample are discussed in great detail with respect to FIG. 2. In some examples, however, one or more protease enzymes are used to digest the protein-containing sample. A protease is an enzyme which is capable of metabolizing (hydrolyzing) peptide bonds in a protein or an oligopeptide to release individual amino acids or smaller protein or oligopeptide fragments. Example proteases include pepsin, trypsin, chymotrypsin, intestinal peptidase, papain, and keratinase.

In one example, the protein-containing sample is first combined with one or more enzymes to simulate gastric digestion within a mammalian subject followed by one or more enzymes to simulate intestinal digestion within the mammalian subject. The enzymes may be selected and conditions controlled to imitate enzymatic breakdown that would normally occur as a protein-containing sample moves through the digestion system of a subject. For example, the enzyme(s) selected to simulate gastric digestion may breakdown the protein-containing sample consistent with how protein in the sample would start digesting in the stomach of a subject when exposed to gastric juices. The enzyme(s) selected to simulate intestinal digestion may further breakdown the protein-containing sample consistent with how protein in the sample would digest after passing from the stomach into the intestinal system of the subject.

Independent of the specific enzyme(s) elected to simulate digestion, the enzyme(s) can be combined with the protein-containing sample (100). In various examples, the enzymes can be combined with the protein-containing sample in beaker, test tube, or other container outside of a living organism. The protein-containing sample can be mixed or blended with the enzyme(s) to initiate interaction between the sample and the enzymes. In some examples, the protein-containing sample is ground or milled (e.g., to a particle size of less than 0.5 millimeters) before being combined with the enzyme(s) to increase the surface area of the sample for enzymatic digestion. Further, to help digest the protein-containing sample, the sample may be mixed with a liquid (e.g., aqueous liquid such as water) either as part of an enzyme solution or as a processing solvent to help breakdown the sample. For example, the enzyme(s) may be dispersed in an aqueous solution that is mixed with the protein-containing sample.

Once combined, enzyme(s) can interact with digestible protein within the protein-containing sample to breakdown the digestible protein component of the protein-containing sample. For example, the enzyme(s) can hydrolyze chemical bonds in the digestible protein, breaking the protein down into polypeptides that are then further broken down into free amino acids. Through this process, a hydrolyzed protein solution can be formed containing, e.g., an aqueous solvent, free amino acids hydrolytically cleaved from protein molecules, and residual undigested protein.

To determine the amount of digestible protein present in the protein-containing sample, the example technique of FIG. 1 includes adding a spectroscopic agent to the hydrolyzed protein solution (102) produced from enzymatic digestion of the protein-containing sample (100). The spectroscopic agent can interact and/or bond with various molecules present in the hydrolyzed protein solution to change the electromagnetic response of the molecules to radiated energy and form a spectroscopic analysis solution. In some examples, for instance, the spectroscopic agent is an optical agent that changes the optical characteristics of the hydrolyzed protein solution to provide an optical measure of the extent of protein digestion in the solution, thereby providing an optical analysis solution.

In general, the spectroscopic agent may be selected to react with molecules present within the hydrolyzed protein solution to measure the amount of amino acids hydrolyzed and released from the protein present in the protein-containing sample during enzymatic digestion (100). The amino acids released from the protein in the sample may represent that portion of the protein that can be digested and metabolized by a mammalian subject upon consumption of the protein-containing sample. The spectroscopic agent may be selected to react with one of two different reaction sites to provide a measure of the amount of amino acid hydrolyzed during enzymatic digestion: the amine group on the amino acid cleaved from the protein molecule or the carboxylic acid group formed on the residual protein backbone after cleaving the peptide bond to release the amino acid.

When amino acid is enzymatically cleaved from a protein backbone, the resulting free amino acid contains an amine functional group where previously joined to the protein while the protein contains a carboxylic acid functional group where previously joined to the amino acid. By adding a spectroscopic agent to the hydrolyzed protein solution that reacts with the amine functional group or the carboxylic acid functional group, the amount of amino acid released during enzymatic digestion can be spectrophotometrically evaluated. For example, a spectroscopic agent that reacts with one of amine functional groups and carboxylic acid functional group can be added to the hydrolyzed protein solution and the solution thereafter spectrophotometrically analyzed.

In instances where the spectroscopic agent added to the hydrolyzed protein solution is intended to bond with amine groups present in the solution, any suitable amine detection reagent can be used. In some examples, the amine detection reagent is selected to be reactive with primary amines present on free amino acids but substantially unreactive with secondary and/or tertiary amines. In other examples, the amine detection reagent can react with both primary amines and secondary and/or tertiary amines. In such applications, the amine detection reagent may preferentially react with primary amines such that the amine detection reagent reacts faster and/or to a greater extent with primary amines present in the hydrolyzed protein solution than secondary and/or tertiary amines present. Example amine detection reagents that can be used as a spectroscopic agent include ninhydrin (2,2-Dihydroxyindane-1,3-dione), dabsyl chloride (4-N,N-dimethylaminoazobenzene-4'-sulfonyl chloride), dansyl chloride (5-(dimethylamino)naphthalene-1-sulfonyl chloride), TNBS (2,4,6-trinitrobenzene sulfonic acid), DABITC (4-N,N'-Dimethylaminoazobenzene-4'-isothiocyanate), MGI (malachite green isothiocyanate) and ISATIN (2,3-indolinedione). In one specific example, ninhydrin is added to the hydrolyzed protein solution as a spectroscopic agent (100).

In other examples where the spectroscopic agent added to the hydrolyzed protein solution is intended to react with the residual protein molecule from which amino acid was released during digestion, the spectroscopic agent may be selected to react with carboxylic acid functional groups. The carboxylic acid functional groups can be formed via hydrolysis of the peptide bond hold the amino acid to the protein molecule during enzymatic digestion. Example carboxylic acid detection reagents that can be used as a spectroscopic agent include phyenacyl bromide, 4-nitrophenol, bromocresol green, and 2-nitrophenylhydrazine.

In practice, the spectroscopic agent may be homogenously mixed or blended into the hydrolyzed protein solution and allowed to react with the molecules present in the solution to form a spectroscopic analysis solution. In applications where an amine detection reagent is used, the reagent may be intermixed with the hydrolyzed protein solution for a period of time sufficient to react substantially all of the primary amines present in the solution.

After adding the spectroscopic agent to the hydrolyzed protein solution (102) to form a spectrophotometric analysis solution, the technique of FIG. 1 further includes spectrophotometrically analyzing the spectrophotometric analysis solution (104). Using a spectrophotometer, the spectrophotometric analysis solution can be irradiated by directing electromagnetic radiation into the solution and measuring the electromagnetic response of the solution. In some examples, the spectrophotometric analysis solution is optically analyzed by directing light (e.g., within the visible, near-ultraviolet, and/or near-infrared spectrum) into the solution and measuring the intensity of the reflection, transmission, emission, and/or absorbance of the light by the solution.

For example, in instances where ninhydrin is used as a spectrophotometric agent, ninhydrin reacts with free primary and secondary amines to produce a deep blue or purple color that absorbs at a wavelength of 570 nanometers (nm). The optical analysis solution produced upon addition of ninhydrin in such applications can be optically analyzed to measure absorbance at 570 nanometers, providing an indication of the amount of reactive amine groups present in the solution. As another example where dabsyl chloride is used as a spectrophotometric agent, dabsyl chloride reacts with free primary and secondary amines to produce a colored derivative that absorbs at wavelengths ranging from 420 nm to 460 nm. The optical analysis solution produced upon addition of dabsyl chloride in such applications can be optically analyzed to measure absorbance within the range from 420 nm to 460 nm, providing an indication of the amount of reactive amine groups present in the solution. As yet another example, where phenacyl bromide is used as the spectrophotometric agent, phenacyl bromide reacts with carboxylic acid functional groups. The optical analysis solution produced upon addition of phenacyl bromide in such applications can be optically analyzed to measure absorbance within the range from 240 nm to 300 nm, providing an indication of the amount of reactive carboxylic acid groups present in the solution.

Although not illustrated in the example of FIG. 1, the spectrophotometric analysis solution can be optionally processed to remove optically interfering macromolecules prior to spectrophotometrically analyzing the solution. Typically, the hydrolyzed protein solution generated through enzymatic digestion of a protein-containing sample will contain free amino acids cleaved from a protein molecules as well as a number of larger macromolecules. These macromolecules may be larger than any amino acid molecule present in the solution and can include undigested protein molecules and residual protein molecules from which free amino acids have been cleaved, such as polypeptides and peptides. If not removed from the spectrophotometric analysis solution prior to analysis, the macromolecules may interfere with analysis of the solution. For example, in instances where the spectrophotometric analysis solution is optically analyzed, the macromolecules may be present in the solution as suspended particulate that can absorb light and prevent the accurate measure of absorbance from reacted optical analysis agent.

To remove optically interfering macromolecules, the optical analysis solution can be filtered or otherwise processed before optical analysis. For instance, in one example, the optical analysis solution is passed through a filter sized to remove substantially all macromolecules that can interfere with optical analysis of free amino acid tagged with an amine detection reagent. In another example, a precipitation agent is added to the optical analysis solution to precipitate out macromolecules present in the solution that can optically interfere with absorbance by amino acids reacted with an optical analysis reagent. The precipitation agent can be added to the optical analysis solution to produce a macromolecule precipitate. Thereafter, the optical analysis solution can be centrifuged to produce a solid pellet containing the precipitated macromolecules and a supernatant liquid containing the amino acids reacted with an optical analysis reagent. The supernatant can be extracted for further optical analysis and quantification of amino acid content. One example precipitation agent that can be used to remove macromolecules from an optical analysis solution is trichloroacetic acid.

In applications where the optical analysis solution is processed to remove macromolecules, the solution can be processed at any suitable time between enzymatic digestion of the protein-containing sample and optical analysis of the solution. For example, the macromolecules can be removed from the hydrated protein solution prior to addition of the spectrophotometric agent. Alternatively, the macromolecules can be removed after addition of the spectrophotometric agent.

While it may be useful to process a spectrophotometric analysis solution to remove macromolecules in some applications, in other examples, removal of the macromolecules is neither necessary nor helpful. For example, in instances where the spectroscopic agent is configured to react with carboxylic acid functional groups, the macromolecules may need to remain within the solution in order to detect the tagged carboxylic acid groups on certain macromolecules from which free amino acid was released during digestion. As another example, in instances in which the spectrometric analysis solution is fluorometrically analyzed, the macromolecules may not interfere with the fluorometric response of the solution.

Accordingly, in some examples, the spectrophotometric analysis solution is spectrophotometrically analyzed (104) according to the technique of FIG. 1 by fluorometrically analyzing the solution. During fluorometry, light at a certain wavelength or range of wavelengths can be emitted into the liquid solution undergoing analysis, causing molecules in the liquid to excite and emit fluorescent emissions at a different wavelength or wavelengths. For example, amine functional groups reacted with an amine detection reagent or carboxylic acid functional groups reacted with a carboxylic acid detection reagent may emit fluorescent emissions in response to being irradiated with light at a certain wavelength or range of wavelengths.

Independent of the specific technique used to spectroscopically analyze the spectroscopic analysis solution (104), the analysis can provide data indicative of the amount of protein digestion that has occurred in the solution undergoing analysis. For example, data from the spectroscopic analysis can provide a value indicative of the concentration of amine groups present in the solution undergoing analysis and/or a value indicative of the concentration of carboxylic acid groups present in the solution undergoing analysis.

As discussed above, reactive amine groups present within a spectroscopic analysis solution (e.g., on amino acid groups released during enzymatic digestion) can react with an amine detection reagent to provide a spectrophotometric response. Additionally or alternatively, reactive carboxylic acid groups present within the spectroscopic analysis solution (e.g., on residual protein molecules from which free amino acid groups were released during enzymatic digestion) can react with a carboxylic acid reagent to provide a spectrophotometric response. Accordingly, the magnitude and/or wavelength of the spectrophotometric response of the solution can vary based on the concentration of reactive amine groups and/or reactive carboxylic acid groups present in the solution. In turn, the concentration of reactive amine groups and/or reactive carboxylic acid groups present in the solution can vary based on the amount of protein-containing sample enzymatically digested and the amount of digestible protein present in the sample.

In practice, the spectrophotometer used to measure the spectrophotometric response of the solution under analysis can measure an output that varies based on the concentration of reactive amine groups and/or reactive carboxylic acid groups present in the solution. In some examples, an optical sensor may direct light at one or more wavelengths into the solution and measure the magnitude and/or frequency of light reflected from the solution, transmitted through (or absorbed by) the solution, and/or the fluorescent emissions generated by the solution. Using calibration data (e.g., stored on the optical sensor), the optical sensor can correlate the magnitude and/or frequency of detected light to a concentration of reactive amine groups in the solution undergoing analysis or a concentration of reactive carboxylic acid groups in the solution. The calibration data can relate the measured optical response of the solution having an unknown concentration of reactive amines and/or reactive carboxylic acid groups to the optical response of one or more solutions having known concentrations of reactive amines and/or carboxylic acid groups. In this manner, the output of the spectrophotometric analysis (104) in the technique of FIG. 1 can be a concentration measurement (e.g., concentration value) that is indicative of the concentration of reactive amines and/or reactive carboxylic acid groups in the spectrophotometric analysis solution having undergone analysis. In various examples, the concentration value can be reported as a weight ratio (e.g., weight of reactive amine or carboxylic acid/weight of protein-containing sample), a mole ratio, a weight concentration, or other suitable value.

To determine an in vivo protein digestibility value, the example technique of FIG. 1 also involves adjusting the measured reactive amine concentration value and/or measured reactive carboxylic acid group value (106). During enzymatic digestion of the protein-containing sample (100), a variety of different amino acids may be cleaved from protein present within the sample. The number of types of amino acids and the amount of each type of amino acid released from the protein will vary depending on the type of protein and quality of protein present within the sample. As a result, the number of reactive amino groups and/or carboxylic acid groups present for reaction with a spectroscopic agent can vary based on the type of protein in the protein-containing sample undergoing analysis.

Amino acids are the individual building blocks of proteins, and each amino acid has a different chemical structure. For example, some amino acids have a single amine group while other amino acids have multiple amine groups. Further, in some amino acids, the amine group is a primary amine while in other amino acids the amine group is a secondary amine. As a result, the number of reactive amines on each amino acid molecule (e.g., those amines that can react with an amine detection reagent) and the relative reactivity of each reactive amine can vary among different amino acids. In general, primary amines react faster and/or to a greater extent with an amine detection reagent than secondary amines. Similarly, amino acids having multiple amino acid groups react with more amine detection reagent (because of the multiple reaction sites) than amino acids with a single amine group. As a result, the spectroscopic response of some amino acids (e.g., those with primary amines and/or multiple amine groups) can be stronger than the spectroscopic response of other amino acids (e.g., those with secondary amines and/or single amine groups). Similar behavior may be exhibited when measuring reactive carboxylic acid groups on the residual protein molecule from which the amino acids were cleaved.

In the techniques of FIG. 1, the measured reactive amine concentration value and/or the measured reactive carboxylic acid group value can be adjusted to determine the number of free amino acid groups released during enzymatic digestion (106). For example, the measured reactive amine concentration value and/or the measured reactive carboxylic acid group value can be adjusted to provide an approximately one-to-one relationship between reactive amine groups and/or reactive carboxylic acid groups and amino acids released during enzymatic digestion. In other words, the measured reactive amine concentration value and/or the measured reactive carboxylic acid group value may be adjusted to account for the stronger spectroscopic response provided by some amino acids (e.g., those with primary amines and/or multiple amine groups) and the weaker spectroscopic response provided by other amino acids (e.g., those with secondary amines and/or single amine groups). The concentration of free amino acids can be determined after adjusting the measured reactive amine concentration value and/or the measured reactive carboxylic acid group value to provide an approximately one-to-one relationship between reactive amine groups and/or reactive carboxylic acid groups and free amino acids. For example, the adjusted amine concentration value and/or adjusted carboxylic acid group concentration value (where provided as a molar concentration) can be set as the amino acid concentration due to the approximately one-to-one relationship.

In one application in accordance with this example, the measured reactive amine concentration value may be decreased based on the concentration of amino acids present having multiple amine groups. Amino acids that have multiple reactive amines include arginine, histidine, and lysine. Additionally or alternatively, the measured reactive amine concentration value may be increased based on the concentration of amino acids present having a secondary amine but no primary amine. Amino acids that have a secondary amine but no primary amine include proline.

The concentration of different amino acids present in the protein-containing sample under analysis (or a specific protein molecule being evaluated for digestibility according the present disclosure) can be determined separately from the technique of FIG. 1. For example, an amino acid analysis can be performed on a different portion of the protein-containing sample from the portion subject to enzymatic digestion according to the example technique of FIG. 1. The amino acid analysis can determine the types of amino acids present in the protein-containing sample and the relative concentration of each type of amino acid in the sample. This amino acid concentration data can provide a measure of the amount of each type of amino acid relative to all amino acids present in the sample. For example, the amino acid concentration data may provide a molar ratio of each type of amino acid relative to all amino acids present in the sample.

With knowledge of the concentration of different amino acids present in the protein-containing sample undergoing analysis, the measured reactive amine concentration value can be adjusted based on the data to provide an adjusted amine concentration value. For example, the measured reactive amine concentration value can be decreased an amount proportional to the concentration of one or more amino acids present in the sample having multiple amine groups and/or increased an amount proportional to the concentration of one or more amino acids present in the sample having a secondary amine but no primary amine. The proportionality constants used to adjust the reactive amine concentration value can be determined empirically of established using literature information on relative reactivity rates.

To determine proportionality constants empirically, a protein-containing sample can be processed according to the technique of FIG. 1 discussed above to provide a measured reactive amine concentration value and/or a measured reactive carboxylic acid group value. A portion of the protein-contain containing sample can separately be digested using standard in vivo digestible protein analysis techniques to provide an in vivo protein digestibility value. For example, the nitrogen content of the sample can be measured before being feed to a mammalian subject (e.g., rat, dog, monkey, human) and the nitrogen content of the subject's excrement also measured. The nitrogen absorbed by the subject can provide a measure of the amount of digestible protein in the sample and, correspondingly, an in vivo protein digestibility value.

Using the measured reactive amine concentration value and/or measured reactive carboxylic acid group value for the sample as well as the in vivo protein digestibility value, the proportionality constants can be determined empirically by iterating values based upon the known mechanism until the best fit with in vivo data for the same sample is obtained.

Independent of the methodology used to determine proportionality constants, in some examples, a measured reactive amine concentration value is increased an amount proportional to the concentration of proline in the protein-containing sample undergoing analysis. The amine group in proline is bound within a pyrrole ring structure, which can inhibit reactivity between the amine group and the amine detection reagent. Additionally or alternatively, the measured reactive amine concentration value may be decreased an amount proportional to the concentration lysine, arginine, and/or histidine present in the protein-containing sample. These amino acids have multiple amine groups and can provide a stronger spectrophotometric response (due to multiple reaction sites with the amine detection reagent).

In one specific example, the measured reactive amine concentration value is adjusted according to the following equation:

$$[adjusted] = [reactive] + \frac{[proline] * C^{proline}}{[lysine] * C^{lysine}} + [arginine] * C^{arginine} + [histidine] * C^{histidine}$$

In the equation above, [adjusted] is the adjusted amine concentration value, [reactive] is the measured reactive amine concentration value, [proline] is a concentration of proline in the protein-containing sample (e.g., as measured by an amino acid analysis performed on the sample), [lysine] is a concentration of lysine in the sample (e.g., as measured by an amino acid analysis performed on the sample), [arginine] is a concentration of arginine in the sample (e.g., as measured by an amino acid analysis performed on the sample), and [histidine] is a concentration of histidine in the sample (e.g., as measured by an amino acid analysis performed on the sample). In addition, $C^{proline}$, $C^{lysine}$, $C^{arginine}$, and $C^{histidine}$ are constants. In some examples, $C^{proline}$, $C^{lysine}$, $C^{arginine}$, and $C^{histidine}$ are empirically determined constants determined by relating samples having known in vivo digestibility values to corresponding known concentrations of reactive amine groups.

In addition to or in lieu of adjusting the measured reactive amine concentration value, the measured reactive carboxylic acid group value may also be adjusted according to the technique of FIG. 1 to provide an adjusted carboxylic acid concentration value. The measured reactive carboxylic acid group value can be adjusted (e.g., increased and/or decreased) an amount proportional to the concentration of one or more amino acids present in the sample. Proportionality constants can be used to adjust the reactive carboxylic acid concentration value. These proportionality constants and can be determined empirically or established using literature information on relative reactivity rates.

In one application in accordance with this example, the measured reactive carboxylic acid concentration value may be decreased based on the concentration of amino acids present having more than one carboxylic acid. Amino acids that have more than one carboxylic acid include aspartic acid and glutamic acid. In some instances where pH conditions are amenable, the phenolic functionality of tyrosine or the sulfhydryl functionalities of cysteine or methionine may additionally react similar to a carboxylic acid group. In such cases, the measured reactive carboxylic acid concentration value may be decreased an amount proportional to the concentration of tyrosine, cysteine, and/or methionine.

In some examples, the measured reactive carboxylic acid group concentration value is decreased an amount proportional to the concentration aspartic acid, glutamic acid, tyrosine, methionine and/or cysteine present in the protein-containing sample. These amino acids have additional nucleophilic functionality and can provide a stronger spectrophotometric response due to higher than one to one reactions with the spectroscopic reagent.

After determining an adjusted amine concentration value and/or adjusted carboxylic acid concentration value (106), the example technique of FIG. 1 further involves determining an in vivo protein digestibility value based on the adjusted amine concentration value and/or adjusted carboxylic acid concentration value. For example, an in vivo protein digestibility value can be determined using empirically established calibration data. The calibration data can be generated by determining adjusted amine concentration and/or adjusted carboxylic acid concentration values for one or more protein-containing samples and also measuring in vivo the protein digestibility of those same protein-containing samples. The determined adjusted amine concentration and/or adjusted carboxylic acid concentration values can then be related to the determined in vivo protein digestibility values.

In some examples, the calibration data takes the form of an equation. The equation can be a single-order equation in slope and Y-intercept form or a higher order polynomial. In one example, the equation is a single-order equation having the formula Y=mX+b, where m is a slope constant and b is a Y-intercept constant. The slope and Y-intercept values can be generated by relating adjusted amine concentration values and/or adjusted carboxylic acid values of protein-containing calibration samples to in vivo protein digestibility values also generated for those calibration samples. The in vivo protein digestibility values can be generated using standard in vivo digestible protein analysis techniques. For example, the nitrogen content of a protein-containing sample can be measured before being feed to a mammalian subject (e.g., rat, dog, monkey, human) and the nitrogen content of the subject's excrement also measured. The nitrogen absorbed by the subject can provide a measure of the amount of digestible protein in the sample and, correspondingly, an in vivo protein digestibility value.

Using the empirically determined calibration data, the adjusted amine concentration value and/or adjusted carboxylic acid concentration value can be converted into an in vivo protein digestibility value, thereby providing a measure of the digestible protein in the protein-containing sample under analysis. The in vivo protein digestibility value so determined may have units of percent of a standard used to calibrate the in vivo system like casein. In some applications, the in vivo protein digestibility value determined using the in vitro process of FIG. 1 is further converted into a protein digestibility corrected amino acid score (PDCAAS). The formula for calculating the PDCAAS percentage is: (mg of limiting amino acid in 1 g of test protein/mg of same amino acid in 1 g of reference protein)×fecal true digestibility percentage. The in vitro protein digestibility value calculated using the technique of FIG. 1 can be used as the fecal true digestibility percentage in the PDCAAS formula.

As briefly discussed above, a variety of different enzymes and enzymatic digestion conditions can be used to enzymatically digest a protein containing sample (step 100 in FIG. 1). FIG. 2 is a flow diagram illustrating an example process for enzymatically digesting a protein-containing sample that can be used in the example technique of FIG. 1.

In the example of FIG. 2, a protein-containing sample is first combined with an enzyme configured to simulate mammalian gastric digestion to provide a simulated gastrically digested sample (200). The enzyme configured to simulate mammalian gastric digestion can be selected to imitate enzymatic breakdown that would normally occur as a protein-containing sample digests in the stomach of a target mammalian subject (e.g., rat, dog, monkey, human) when exposed to gastric juices. In one application of the technique of FIG. 2, the enzyme pepsin is used to simulate mammalian gastric digestion.

The technique of FIG. 2 further includes adjusting the pH of a solution containing the protein-containing sample and the enzyme configured to simulate mammalian gastric digestion (202). The pH of the solution may be adjusted to a range corresponding to a pH typically found within the stomach of a target mammalian subject for which protein digestibility is being evaluated in vitro. This can help ensure that the activity of the enzyme replicates what would occur in vivo. In some examples, an acidic reagent (e.g., HCl) is added to the solution to reduce the pH to a pH less than 4, such as a pH ranging from 2 to 4. In different examples, the pH can be adjusted before combining the protein-containing sample with the enzyme (e.g., by adding the acidic reagent to either the sample or the enzyme) or after combining the protein-containing reagent with the enzyme. Therefore, although FIG. 2 illustrates an example process sequence, it should be appreciated that the disclosure is not limited in this respect.

The technique of FIG. 2 further includes adjusting the temperature of the solution containing the protein-containing sample and the enzyme configured to simulate mammalian gastric digestion and incubating the sample for a period of time (204). The temperature of the solution may be adjusted to a range corresponding to a temperature typically found within the stomach of a target mammalian subject for which protein digestibility is being evaluated in vitro. For example, the temperature of the solution may be adjusted to a range corresponding to the average temperature of a mammalian body (e.g., from 35 degrees Celsius to 40 degrees Celsius). Further, the incubation time can be selected to replicate the amount of time the protein-containing sample would be expected to remain in the stomach of the target mammalian subject upon ingestion. In some examples, the solution containing the protein-containing sample and the enzyme configured to simulate mammalian gastric digestion are incubated for period ranging from 5 minutes to 2 hours, such as a period ranging from 30 minutes to 90 minutes.

After incubating the protein-containing sample to produce a gastrically-digested sample, the pH of the gastrically-digested sample is further adjusted in the technique of FIG. 2 (206). For example, the pH of the gastrically-digested sample may be adjusted to a pH that substantially or entirely terminates activity of the enzyme configured to simulate mammalian gastric digestion, preparing the gastrically-digested sample for simulated intestinal digestion. The pH of the gastrically-digested sample may be adjusted to a range corresponding to a pH typically found within the intestinal system of the target mammalian subject for which protein digestibility is being evaluated in vitro. In some examples, a basic reagent (e.g., NaOH) is added to the gastrically-digested sample to increase the pH to a pH greater than 4, such as a pH ranging from 6 to 8.

The technique of FIG. 2 also includes adding an enzyme configured to simulate mammalian intestinal digestion to the gastrically-digested sample (208). The enzyme configured to simulate mammalian intestinal digestion can be selected to imitate enzymatic breakdown that would normally occur as a protein-containing sample digests in the intestinal system of the target mammalian subject. In one application of the technique of FIG. 2, the enzymes trypsin and/or chymotrypsin are used to simulate mammalian intestinal digestion.

In addition to adding the enzyme configured to simulate mammalian intestinal digestion to the gastrically-digested sample (208), the technique of FIG. 2 also includes incubating the gastrically-digested sample containing the enzyme configured to simulate mammalian intestinal digestion (210). The temperature of the gastrically-digested sample containing the enzyme may be controlled to a range corresponding to a temperature typically found within the intestinal system of the target mammalian subject for which protein digestibility is being evaluated in vitro (e.g., from 35 degrees Celsius to 40 degrees Celsius). Further, the incubation time can be selected to replicate the amount of time the gastrically-digested sample containing the enzyme would be expected to remain in the intestinal system of the target mammalian subject upon ingestion. In some examples, the gastrically-digested sample containing the enzyme is incubated for period greater than 2 hours, such as a period ranging from 3 hours to 5 hours.

The intestinally-digested sample produced through the technique of FIG. 2 can be further analyzed following the methodology discussed above with respect to FIG. 1. In some applications, the intestinally-digested sample is chilled (e.g., flash frozen using liquid nitrogen) at the end of the end of the incubation period (212). Rapidly chilling the intestinally-digested sample can terminate enzymatic activity and prepare the sample for follow-on analysis.

The techniques described in this disclosure may be implemented, at least in part, in hardware, software, firmware or any combination thereof. For example, various aspects of the described techniques may be implemented within one or more processors (e.g., one or more processors associated with an optical sensor and/or fiber determination computer program), including one or more microprocessors, digital signal processors (DSPs), application specific integrated circuits (ASICs), field programmable gate arrays (FPGAs), or any other equivalent integrated or discrete logic circuitry, as well as any combinations of such components. A control unit comprising hardware may also perform one or more of the techniques of this disclosure.

Such hardware, software, and firmware may be implemented within the same device or within separate devices to support the various operations and functions described in this disclosure. In addition, any of the described components (e.g., optical sensor) may be implemented together or separately as discrete but interoperable logic devices.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following example may provide additional details about digestible protein determination in accordance with this disclosure.

EXAMPLE

Eight different protein-containing products were obtained and tested consistent with the techniques of the present disclosure to develop adjusted amine concentration values and corresponding in vitro digestibility scores. The eight products were as follows: sunflower seeds, lentils, rolled oats, split peas, kidney beans, black eyed peas, and casein.

First, a sample of each product was enzymatically digested to simulate gastric digestion. Five hundred grams of each sample were added to a test tube containing 20 ml of HCl to adjust the pH of the sample down to approximately 2.0. Each sample was incubated at this reduced pH for 30 minutes at a temperature of 37 degrees Celsius. Subsequently, 8 mg of the enzyme pepsin were added to each sample and allowed to incubate for 60 minutes at a temperature of 37 degrees Celsius. After completing incubation, the pH of the sample was raised to pH 7.4 using NaOH to terminate the activity of pepsin and to facilitate the intestinal digestion.

Subsequently, 10 mg of the enzyme trypsin and 10 mg of the enzyme chymotrypsin were added to each sample at the adjusted pH of 7.4 to simulate intestinal digestion. Each sample containing the trypsin and chymotrypsin was then incubated for 4 hours at a temperature of 37 degrees Celsius. At the end of incubation, the reaction mixture was flash frozen using liquid nitrogen to terminate all enzymatic activity.

To continue with the process, each frozen sample was thawed to room temperature and trichloroacetic acid (TCA) precipitation was carried out to remove any source of macromolecules (e.g., proteins, polypeptides and peptides) that could contribute to an increased level of estimated reactive amines. In particular, 1 volume of 40% TCA solution was added to 4 volumes of each digested protein sample and the samples incubated for approximately 16 hours at a temperature of 4 degrees Celsius. Thereafter, the samples were centrifuged and a clear supernatant extracted for further analysis.

To determine the number of reactive amines in each sample, 125 microliters (µl) of each supernatant was combined with 94 µl of ninhydrin solution. The mixture was incubated for approximately 30 minutes at a temperature of 70 degrees Celsius. Thereafter, the absorbance of the samples was measured at a wavelength of 570 nanometers and reactive amine concentration determined using stored calibration data corresponding to that absorbance wavelength. The following tables show the determined reactive amine concentration values for the samples.

| | Sunflower seeds | Lentils | Rolled Oats | Split Peas | Kidney Beans |
|---|---|---|---|---|---|
| Determined Reactive Amine Concentration (mM) | 5.359 | 5.553 | 2.491 | 5.276 | 2.75 |

| | Whole Wheat | Black Eyed Peas | Casein |
|---|---|---|---|
| Determined Reactive Amine Concentration (mM) | 3.045 | 4.444 | 7.938 |

Separately, an amino acid analysis was performed on each of the protein-containing samples to determine the types of amino acids present in each sample and the relative concentration of each type of amino acid in the sample. The following tables show the results of the amino acid analysis, where the results are reported as weight percentages of each amino acid (as measured on a dry-weight basis) relative to the total weight of the sample.

| Amino Acid | Sunflower seeds (wt %) | Lentils (wt %) | Rolled Oats (wt %) | Split Peas (wt %) | Kidney Beans (wt %) |
|---|---|---|---|---|---|
| L-HydroxyProline | 0.00 | 0.00 | 0.00 | 0.00 | 0.00 |
| L-Aspartic acid | 1.62 | 2.05 | 0.81 | 2.07 | 2.03 |
| L-Threonine | 0.64 | 0.65 | 0.34 | 0.66 | 0.69 |
| L-Serine | 0.70 | 0.80 | 0.46 | 0.77 | 0.86 |
| L-Glutamic Acid | 3.23 | 2.88 | 2.15 | 3.09 | 2.70 |
| L-Proline | 0.70 | 0.71 | 0.53 | 0.71 | 0.61 |
| L-Glycine | 0.85 | 0.63 | 0.46 | 0.70 | 0.59 |
| L-Alanine | 0.65 | 0.68 | 0.44 | 0.70 | 0.64 |
| L-Valine | 0.88 | 0.83 | 0.55 | 0.80 | 0.96 |
| L-Isoleucine | 0.74 | 0.79 | 0.39 | 0.79 | 0.77 |
| L-Leucine | 1.10 | 1.32 | 0.77 | 1.31 | 1.32 |
| L-Tyrosine | 0.57 | 0.61 | 0.41 | 0.69 | 0.59 |
| L-Phenylalanine | 0.90 | 0.95 | 0.55 | 0.93 | 1.01 |
| L-Lysine | 0.62 | 1.29 | 0.43 | 1.38 | 1.20 |
| L-Histidine | 0.46 | 0.45 | 0.24 | 0.46 | 0.52 |
| L-Arginine | 1.59 | 1.47 | 0.73 | 1.63 | 1.07 |
| Total | 15.24 | 16.10 | 9.26 | 16.68 | 15.55 |

| Amino Acid | Whole Wheat (wt %) | Black Eyed Peas (wt %) | Casein (wt %) |
|---|---|---|---|
| L-HydroxyProline | 0.00 | 0.00 | 0.00 |
| L-Aspartic acid | 0.46 | 2.00 | 5.24 |
| L-Threonine | 0.26 | 0.67 | 2.97 |
| L-Serine | 0.40 | 0.78 | 3.00 |
| L-Glutamic Acid | 2.71 | 0.31 | 16.14 |
| L-Proline | 0.86 | 0.71 | 7.61 |
| L-Glycine | 0.33 | 0.62 | 1.20 |
| L-Alanine | 0.29 | 0.68 | 2.01 |
| L-Valine | 0.40 | 0.85 | 4.79 |
| L-Isoleucine | 0.31 | 0.77 | 4.01 |
| L-Leucine | 0.60 | 1.35 | 7.00 |
| L-Tyrosine | 0.29 | 0.64 | 4.50 |
| L-Phenylalanine | 0.44 | 1.04 | 4.00 |
| L-Lysine | 0.26 | 1.23 | 6.34 |
| L-Histidine | 0.21 | 0.58 | 2.14 |
| L-Arginine | 0.47 | 1.28 | 2.79 |
| Total | 8.30 | 13.49 | 73.74 |

Continuing with the analysis, an adjusted amine concentration value was determined using the amino acid concentration data in the tables above as well as the determined reactive amine concentration values for the samples. In particular, the determined reactive amine concentration value for each sample was adjusted according to the following equation:

$$[\text{adjusted}] = [\text{reactive}] + \frac{[\text{proline}] * C^{proline}}{[\text{lysine}] * C^{lysine}} + [\text{arginine}] * C^{arginine} + [\text{histidine}] * C^{histidine}$$

Using the equation above, the adjusted amine concentration value ([adjusted]) for each sample was calculated using the determined reactive amine concentration value ([reactive]) for each sample, the concentration of proline ([proline]) in each sample, the concentration of lysine ([lysine]) in each sample, the concentration of arginine ([arginine]) in each sample, and the concentration of histidine ([histidine]) in each sample. The constants used in the calculation were empirically determined and were as follows: $C^{proline}=20$, $C^{lysine}=5$, $C^{arginine}=2$, and $C^{histidine}=2$. The resulting determined adjusted amine concentration values for the samples are as follows:

| | Sunflower seeds | Lentils | Rolled Oats | Split Peas | Kidney Beans |
|---|---|---|---|---|---|
| Adjusted Amine Concentration (mM) | 13.93 | 11.58 | 9.43 | 11.52 | 7.98 |

| | Whole Wheat | Black Eyed Peas | Casein |
|---|---|---|---|
| Adjusted Amine Concentration (mM) | 17.44 | 10.47 | 22.59 |

For comparative purposes, a relative digestibility value (also referred to as an in vitro digestibility score) was calculated based on the adjusted amine concentration value of the casein sample. Casein is reported as having a protein digestibility corrected score of 1.00 according to standard in vivo testing methods. Accordingly, an in vitro digestibility score was calculated by dividing the adjusted amine concentration value by the adjusted amine concentration value for casein. It was believed this in vitro digestibility score might provide a suitable proxy for in vivo digestibility of the samples. The results are as follows:

| | Sunflower seeds | Lentils | Rolled Oats | Split Peas | Kidney Beans |
|---|---|---|---|---|---|
| In Vitro Digestibility Score | 0.62 | 0.51 | 0.42 | 0.51 | 0.35 |

| | Whole Wheat | Black Eyed Peas | Casein |
|---|---|---|---|
| In Vitro Digestibility Score | 0.77 | 0.46 | 1.00 |

To develop an in vivo protein digestibility calibration equation, the adjusted amine concentration values for the eight samples were correlated to literature-reported in vivo protein digestibility values. The data is summarized in the following table:

| Sample | Adjusted Amine Concentration (mM) | Literature-Reported In Vivo Protein Digestibility Value |
|---|---|---|
| Casein | 22.59 | 100 |
| Sunflower seeds | 13.93 | 94 |
| Lentils | 11.58 | 86 |
| Rolled Oats | 9.43 | 83 |
| Split Peas | 11.52 | 84 |
| Kidney Beans | 7.98 | 81 |
| Whole Wheat | 17.44 | 91 |
| Black Eyed Peas | 10.47 | 84 |

Subsequently, the data in the table above was plotted with the literature values on the Y-axis and the adjusted amine concentration values on the X-axis. A single-order curve was fitted to the data having the formula Y=mX+b, where m was determined to be 1.28, and Y was determined to 71.09.

The invention claimed is:

1. A method comprising:
combining a sample containing a protein with at least one enzyme configured to simulate mammalian protein digestion, thereby at least partially hydrolyzing the protein and producing therefrom a hydrolyzed protein solution;
adding a spectroscopic agent to the hydrolyzed protein solution that reacts with at least one of amine terminal and carboxylic terminal groups in the hydrolyzed protein solution, thereby forming a spectroscopic analysis solution;
spectroscopically analyzing the spectroscopic analysis solution and determining therefrom a value indicative of at least one of a concentration of reactive amine groups in the spectroscopic analysis solution and a concentration of reactive carboxylic acid groups in the spectroscopic analysis solution;
increasing or decreasing the value indicative of at least one of the concentration of reactive amine groups and the concentration of reactive carboxylic acid groups using amino acid concentration data for an amino acid selected from the group consisting of proline, lysine, arginine, histidine, serine, aspartic acid, glutamic acid, cysteine, tyrosine, and combinations thereof from the sample to calculate at least one of an adjusted amine concentration value and an adjusted carboxylic acid concentration value; and
determining an in vivo protein digestibility value for the sample based on the at least one of the adjusted amine concentration value and the adjusted carboxylic acid concentration value using data that relates adjusted amine concentration values or adjusted carboxylic acid concentration values to in vivo protein digestibility values.

2. The method of claim 1, wherein increasing or decreasing the value indicative of at least one of the concentration of reactive amine groups and the concentration of reactive carboxylic acid groups comprises increasing or decreasing a value indicative of the concentration of reactive amine groups to increase the value in an amount proportional to a concentration of proline in the sample.

3. The method of claim 1, wherein increasing or decreasing the value indicative of at least one of the concentration of reactive amine groups and the concentration of reactive carboxylic acid groups comprises increasing or decreasing a value indicative of the concentration of reactive amine groups to decrease the value in an amount proportional to a concentration of lysine in the sample.

4. The method of claim 1, wherein increasing or decreasing the value indicative of at least one of the concentration of reactive amine groups and the concentration of reactive carboxylic acid groups comprises increasing or decreasing a value indicative of the concentration of reactive amine groups to decrease the value in an amount proportional to a concentration of histidine and a concentration of arginine in the sample.

5. The method of claim 1, wherein increasing or decreasing the value indicative of at least one of the concentration of reactive amine groups and the concentration of reactive carboxylic acid groups comprises increasing or decreasing a value indicative of the concentration of reactive amine groups according to the formula:

$$[\text{adjusted}] = [\text{reactive}] + \frac{[\text{proline}] * C^{proline}}{[\text{lysine}] * C^{lysine}} + [\text{arginine}] * C^{arginine} + [\text{histidine}] * C^{histidine}$$

wherein [adjusted] is the adjusted amine concentration value, [reactive] is the value indicative of the concentration of reactive amine groups, [proline] is a concentration of proline in the sample, [lysine] is a concentration of lysine in the sample, [arginine] is a concentration of arginine in the sample, [histidine] is a concentration of histidine in the sample, and $C^{proline}$, $C^{lysine}$, $C^{arginine}$, and $C^{histidine}$ are empirically determined constants determined by relating samples having known in vivo protein digestibility values to corresponding known concentrations of reactive amine groups.

6. The method of claim 1, wherein increasing or decreasing the value indicative of at least one of the concentration of reactive amine groups and the concentration of reactive carboxylic acid groups comprises increasing or decreasing a value indicative of the concentration of the reactive carboxylic acid groups to decrease the value in an amount proportional to a concentration of serine in the sample.

7. The method of claim 1, wherein increasing or decreasing the value indicative of at least one of the concentration of reactive amine groups and the concentration of reactive carboxylic acid groups comprises increasing or decreasing a value indicative of the concentration of the reactive carboxylic acid groups to decrease the value in an amount proportional to a concentration of aspartic acid in the sample.

8. The method of claim 1, wherein increasing or decreasing the value indicative of at least one of the concentration of reactive amine groups and the concentration of reactive carboxylic acid groups comprises increasing or decreasing a value indicative of the concentration of the reactive carboxylic acid groups to decrease the value in an amount proportional to a concentration of glutamic acid in the sample.

9. The method of claim 1, wherein increasing or decreasing the value indicative of at least one of the concentration of reactive amine groups and the concentration of reactive carboxylic acid groups comprises increasing or decreasing a value indicative of the concentration of the reactive carboxylic acid groups to decrease the value in an amount proportional to a concentration of cysteine in the sample.

10. The method of claim 1, wherein increasing or decreasing the value indicative of at least one of the concentration of reactive amine groups and the concentration of reactive carboxylic acid groups comprises increasing or decreasing a value indicative of the concentration of the reactive carboxylic acid groups to decrease the value in an amount proportional to a concentration of tyrosine in the sample.

11. The method of claim 1, wherein the spectroscopic agent is configured to react with amine terminal groups and is selected from the group consisting of ninhydrin, dabsyl chloride, dansyl chloride, TNBS (2,4,6-trinitrobenzene sulfonic acid), DABITC (4-N,N'-Dimethylaminoazobenzene-4'-isothiocyanate), MGI (malachite green isothiocyanate) and ISATIN (2,3-indolinedione), and wherein spectroscopically analyzing the spectroscopic analysis solution comprises spectroscopically analyzing the spectroscopic analysis solution and determining therefrom a value indicative of a concentration of reactive amine groups.

12. The method of claim 1, wherein the spectroscopic agent is configured to react with carboxylic terminal groups and comprises one of phenacyl bromide, 4-nitrophenol, bromocresol green, and 2-nitrophenylhydrazine, and wherein spectroscopically analyzing the spectroscopic analysis solution comprises spectroscopically analyzing the spectroscopic analysis solution and determining therefrom a value indicative of a concentration of reactive carboxylic acid groups.

13. The method of claim 1, wherein spectroscopically analyzing the spectroscopic analysis solution comprises fluorometrically analyzing the spectroscopic analysis solution.

14. The method of claim 1, further comprising, subsequent to adding the spectroscopic agent and prior to spectroscopically analyzing the spectroscopic analysis solution, precipitating out macromolecules present in the spectroscopic analysis solution and removing a precipitate from the spectroscopic analysis solution.

15. The method of claim 1, wherein combining the sample containing the protein with at least one enzyme configured to simulate mammalian protein digestion comprises combining the sample with an enzyme configured to simulate mammalian gastric digestion and subsequently combining the sample with an enzyme configured to simulate mammalian intestinal digestion.

16. The method of claim 15, wherein the enzyme configured to simulate mammalian gastric digestion comprises pepsin and the enzyme configured to simulate mammalian intestinal digestion comprises trypsin and chymotrypsin.

17. The method of claim 15,
wherein combining the sample with the enzyme configured to simulate mammalian gastric digestion comprises adjusting a pH of a solution containing the sample and the enzyme configured to simulate mammalian gastric digestion to a pH less than 4, and incubating the solution containing the sample and the enzyme configured to simulate mammalian gastric digestion at a temperature ranging from 35 degrees Celsius to 40 degrees Celsius; and
wherein combining the sample with the enzyme configured to simulate mammalian intestinal digestion comprises, prior to combining the sample with the enzyme configured to simulate mammalian intestinal digestion, adjusting the pH of the solution to a range from 6 to 8, and, subsequent to combining the sample with the enzyme configured to simulate mammalian intestinal digestion, incubating a solution containing the sample and the enzyme configured to simulate mammalian intestinal digestion at a temperature ranging from 35 degrees Celsius to 40 degrees Celsius.

18. The method of claim 1, wherein determining the in vivo protein digestibility value for the sample comprises calculating the in vivo protein digestibility value using an equation generated by relating samples having known in vivo protein digestibility values to known adjusted amine concentration values or known adjusted carboxylic acid values.

19. The method of claim 1, further comprising calculating a protein digestibility corrected amino acid score using the determined in vivo protein digestibility value.

20. The method of claim 1, wherein the data relating adjusted amine concentration values or adjusted carboxylic acid concentration values to in vivo protein digestibility values comprises data relating adjusted amine concentration values or adjusted carboxylic acid concentration values to in vivo protein digestibility values generated using a rat subject to provide in vivo protein digestibility values.

21. The method of claim 1, wherein the sample containing the protein comprises a human-consumable product.

22. A method comprising:
mixing a sample containing a protein with pepsin to simulate mammalian gastric digestion and generating therefrom a simulated gastrically digested sample;
mixing the simulated gastrically digested sample with trypsin and chymotrypsin to simulate mammalian intestinal digestion and generating therefrom a simulated intestinally digested sample;
adding a spectroscopic agent to the simulated intestinally digested sample that reacts with at least one of amine terminal and carboxylic terminal groups in the simulated intestinally digested sample, thereby forming an optical analysis solution;
optically analyzing the optical analysis solution and determining therefrom a value indicative of at least one of a concentration of reactive amine groups in the optical analysis solution and a concentration of reactive carboxylic acid groups in the optical analysis solution;
increasing or decreasing the value indicative of at least one of the concentration of reactive amine groups and the concentration of reactive carboxylic acid groups using amino acid concentration data for an amino acid selected from the group consisting of proline, lysine, arginine, histidine, aspartic acid, glutamic acid, cysteine, tyrosine, and combinations thereof from the sample to calculate at least one of an adjusted amine concentration value and an adjusted carboxylic acid concentration value; and
determining an in vivo protein digestibility value for the sample based on the at least one of the adjusted amine concentration value and the adjusted carboxylic acid concentration value using data that relates adjusted amine concentration values or adjusted carboxylic acid values to in vivo protein digestibility values.

23. The method of claim 22, wherein the spectroscopic agent is configured to react with amine terminal groups and comprises one of ninhydrin, dabsyl chloride, and dansyl chloride.

24. The method of claim 23, wherein increasing or decreasing the value indicative of at least one of the concentration of reactive amine groups and the concentration of reactive carboxylic acid groups comprises increasing or decreasing a value indicative of the concentration of reactive amine groups to increase the concentration of reactive amine groups in an amount proportional to a concentration of proline in the sample and decrease the concentration of reactive amine groups in an amount proportional to a concentration of lysine, a concentration of histidine, and a concentration of arginine in the sample.

25. The method of claim 24, wherein increasing or decreasing the value indicative of the concentration of the reactive amine groups comprises increasing or decreasing the value according to the formula:

$$[\text{adjusted}] = [\text{reactive}] + \frac{[\text{proline}] * C^{proline}}{[\text{lysine}] * C^{lysine}} + [\text{arginine}] * C^{arginine} + [\text{histidine}] * C^{histidine}$$

wherein [adjusted] is the adjusted amine concentration value, [reactive] is the value indicative of the concentration of reactive amine groups, [proline] is a concentration of proline in the sample, [lysine] is a concentration of lysine in the sample, [arginine] is a concentration of arginine in the sample, [histidine] is a concentration of histidine in the sample, and $C^{proline}$, $C^{lysine}$, $C^{arginine}$, and $C^{histidine}$ are empirically determined constants relating samples having known in vivo protein digestibility values to corresponding known concentrations of reactive amine groups.

26. The method of claim 22, wherein the spectroscopic agent is configured to react with carboxylic terminal groups and comprises one of phenacyl bromide and 4-nitrophenol.

27. The method of claim 26, wherein increasing or decreasing the value indicative of at least one of the concentration of reactive amine groups and the concentration of reactive carboxylic acid groups comprises increasing or decreasing a value indicative of the concentration of the reactive carboxylic acid groups to decrease the concentration in an amount proportional to a concentration of aspartic acid and a concentration of glutamic acid in the sample.

28. The method of claim 22, further comprising:
adjusting a pH of the simulated gastrically digested sample to a pH less than 4, and incubating the simulated gastrically digested sample at a temperature ranging from 35 degrees Celsius to 40 degrees Celsius for a period ranging from 30 minutes to 90 minutes;
subsequent to incubating the simulated gastrically digested sample, adjusting the pH of the simulated gastrically digested sample to a range from 6 to 8 and thereafter mixing the simulated gastrically digested sample with trypsin and chymotrypsin, and
incubating the simulated intestinally digested sample at a temperature ranging from 35 degrees Celsius to 40 degrees Celsius for a period ranging from 3 hours to 5 hours.

29. The method of claim 28, further comprising, subsequent to adding the spectroscopic agent and prior to optically analyzing the optical analysis solution, precipitating out macromolecules present in the optical analysis solution and removing a precipitate from the optical analysis solution.

* * * * *